(12) United States Patent
Bourget et al.

(10) Patent No.: US 8,731,656 B2
(45) Date of Patent: May 20, 2014

(54) CLOSED-LOOP THERAPY ADJUSTMENT

(75) Inventors: Duane L. Bourget, Albertville, MN (US); Keith A. Miesel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/154,309

(22) Filed: Jun. 6, 2011

(65) Prior Publication Data

US 2011/0238130 A1 Sep. 29, 2011

Related U.S. Application Data

(63) Continuation of application No. 11/607,426, filed on Dec. 1, 2006, now Pat. No. 7,957,797.

(60) Provisional application No. 60/742,044, filed on Dec. 2, 2005.

(51) Int. Cl.
*A61N 1/00* (2006.01)

(52) U.S. Cl.
USPC .............................................. 607/2

(58) Field of Classification Search
USPC ......... 607/17, 30, 62; 600/481, 529, 544, 546
See application file for complete search history.

(56) References Cited

U.S. PATENT DOCUMENTS

| | | |
|---|---|---|
| 4,543,955 A | 10/1985 | Schroeppel |
| 5,031,618 A | 7/1991 | Mullett |
| 5,058,584 A | 10/1991 | Bourgeois |
| 5,312,446 A | 5/1994 | Holschbach et al. |
| 5,342,409 A | 8/1994 | Mullett |
| 5,487,755 A | 1/1996 | Snell et al. |
| 5,513,645 A | 5/1996 | Jacobson et al. |
| 5,558,640 A | 9/1996 | Pfeiler et al. |
| 5,593,431 A | 1/1997 | Sheldon |

(Continued)

FOREIGN PATENT DOCUMENTS

| | | |
|---|---|---|
| EP | 0 613 390 B1 | 10/2000 |
| WO | WO 94/05371 | 3/1994 |

(Continued)

OTHER PUBLICATIONS

Office Action dated Jul. 10, 2012 for U.S. Appl. No. 12/966,827, (9 pgs.).

(Continued)

*Primary Examiner* — Christopher D Koharski
*Assistant Examiner* — Roland Dinga
(74) *Attorney, Agent, or Firm* — Shumaker & Sieffert, P.A.

(57) ABSTRACT

Techniques for detecting a value of a sensed patient parameter, and automatically delivering therapy to a patient according to therapy information previously associated with the detected value, are described. In exemplary embodiments, a medical device receives a therapy adjustment from the patient. In response to the adjustment, the medical device associates a sensed value of a patient parameter with therapy information determined based on the adjustment. Whenever the parameter value is subsequently detected, the medical device delivers therapy according to the associated therapy information. In this manner, the medical device may "learn" to automatically adjust therapy in the manner desired by the patient as the sensed parameter of the patient changes. Exemplary patient parameters that may be sensed for performance of the described techniques include posture, activity, heart rate, electromyography (EMG), an electroencephalogram (EEG), an electrocardiogram (ECG), temperature, respiration rate, and pH.

20 Claims, 11 Drawing Sheets

(56) References Cited

U.S. PATENT DOCUMENTS

| | | | |
|---|---|---|---|
| 5,628,317 | A | 5/1997 | Starkebaum et al. |
| 5,720,770 | A | 2/1998 | Nappholz et al. |
| 5,832,932 | A | 11/1998 | Elsberry et al. |
| 5,836,989 | A | 11/1998 | Shelton |
| 5,893,883 | A | 4/1999 | Torgerson et al. |
| 5,895,371 | A | 4/1999 | Levitas et al. |
| 5,904,708 | A | 5/1999 | Goedeke |
| 5,938,690 | A | 8/1999 | Law et al. |
| 5,941,906 | A | 8/1999 | Barreras, Sr. et al. |
| 5,944,680 | A | 8/1999 | Christopherson et al. |
| 6,027,456 | A | 2/2000 | Feler et al. |
| 6,099,479 | A | 8/2000 | Christopherson et al. |
| 6,120,467 | A | 9/2000 | Schallhorn |
| 6,308,099 | B1 | 10/2001 | Fox et al. |
| 6,327,501 | B1 | 12/2001 | Levine et al. |
| 6,341,236 | B1 | 1/2002 | Osorio et al. |
| 6,381,496 | B1 | 4/2002 | Meadows et al. |
| 6,440,090 | B1 | 8/2002 | Schallhorn |
| 6,466,821 | B1 | 10/2002 | Pianca et al. |
| 6,609,031 | B1 | 8/2003 | Law et al. |
| 6,620,151 | B2 | 9/2003 | Blischak et al. |
| 6,635,048 | B1 | 10/2003 | Ullestad et al. |
| 6,659,968 | B1 | 12/2003 | McClure |
| 6,748,276 | B1 | 6/2004 | Daignault, Jr. et al. |
| 6,832,113 | B2 | 12/2004 | Belalcazar |
| 6,997,882 | B1 | 2/2006 | Parker et al. |
| 7,130,689 | B1 | 10/2006 | Turcott |
| 7,162,304 | B1 | 1/2007 | Bradley |
| 7,313,440 | B2 * | 12/2007 | Miesel .......................... 607/19 |
| 2002/0038137 | A1 | 3/2002 | Stein |
| 2002/0107553 | A1 | 8/2002 | Hill et al. |
| 2002/0115939 | A1 | 8/2002 | Mulligan et al. |
| 2002/0165586 | A1 | 11/2002 | Hill et al. |
| 2003/0065370 | A1 | 4/2003 | Lebel et al. |
| 2003/0171791 | A1 | 9/2003 | KenKnight et al. |
| 2003/0181960 | A1 | 9/2003 | Carter et al. |
| 2004/0088020 | A1 | 5/2004 | Condie et al. |
| 2004/0102814 | A1 | 5/2004 | Sorensen et al. |
| 2004/0199215 | A1 | 10/2004 | Lee et al. |
| 2004/0199216 | A1 | 10/2004 | Lee et al. |
| 2004/0199217 | A1 | 10/2004 | Lee et al. |
| 2004/0199218 | A1 | 10/2004 | Lee et al. |
| 2004/0215286 | A1 | 10/2004 | Stypulkowski |
| 2004/0220621 | A1 | 11/2004 | Zhou et al. |
| 2005/0043767 | A1 | 2/2005 | Belalcazar |
| 2005/0060001 | A1 * | 3/2005 | Singhal et al. .................. 607/19 |
| 2005/0209645 | A1 * | 9/2005 | Heruth et al. ..................... 607/3 |
| 2005/0222638 | A1 | 10/2005 | Foley et al. |
| 2005/0240242 | A1 | 10/2005 | DiLorenzo |
| 2005/0245988 | A1 | 11/2005 | Miesel |
| 2005/0283210 | A1 | 12/2005 | Blischak et al. |
| 2006/0212080 | A1 | 9/2006 | Hartley et al. |
| 2006/0235472 | A1 | 10/2006 | Goetz et al. |

FOREIGN PATENT DOCUMENTS

| | | |
|---|---|---|
| WO | WO 96/29007 | 9/1996 |
| WO | WO 99/56820 | 11/1999 |
| WO | WO 2005/102499 | 11/2005 |

OTHER PUBLICATIONS

Velten, et al. "A New Three-Axis Accelerometer," Sensor '99—9$^{th}$ Int'l Traide Fair and Conference for Sensors/Transducers & Systems, Nürnberg, Germany, May 18-20, 1999. Sensor '99 Proceedings II, 1999, A 5.2, pp. 47-52.

Notification of Transmittal of the International Preliminary Report on Patentability dated Feb. 29, 2008 for application No. PCT/US2006/046087 (11 pgs.).

Notification of Transmittal of the International Preliminary Report on Patentability dated Feb. 29, 2008 for application No. PCT/US2006/046061 (11 pgs.).

European Office Action dated Sep. 3, 2010 for Application No. 06 844 725.9-1269 (5 pgs.).

European Office Action dated Sep. 3, 2010 for Application No. 06 844 740.8-1269 (5 pgs.).

Office Action dated Feb. 22, 2010 for U.S. Appl. No. 11/414,625 (9 pgs.).

Responsive Amendment dated May 24, 2010 for U.S. Appl. No. 11/414,625 (19 pgs.).

Responsive Amendment dated Apr. 27, 2009 for U.S. Appl. No. 10/691,917 (16 pgs.).

Office Action dated Dec. 28, 2009 for U.S. Appl. No. 10/691,917 (7 pgs.).

Response dated Feb. 26, 2010 for U.S. Appl. No. 10/691,917 (6 pgs.).

Responsive Amendment dated Nov. 23, 2009 for U.S. Appl. No. 11/414,625 (18 pgs.).

Office Action dated Aug. 21, 2008 for U.S. Appl. No. 10/691,917 (9 pgs.).

Responsive Amendment dated Feb. 27, 2008 for U.S. Appl. No. 10/691,917 (16 pgs.).

Office Action dated Dec. 28, 2007 for U.S. Appl. No. 10/691,917 (8 pgs.).

Responsive Amendment dated Oct. 9, 2007 for U.S. Appl. No. 10/691,917 (16 pgs.).

Office Action dated Jul. 9, 2007 for U.S. Appl. No. 10/691,917 (7 pgs.).

Responsive Amendment dated Mar. 12, 2007 for U.S. Appl. No. 10/691,917 (17 pgs.).

Office Action dated Dec. 27, 2006 for U.S. Appl. No. 10/691,917 (5 pgs.).

Responsive Amendment dated Dec. 12, 2006 for U.S. Appl. No. 10/691,917 (15 pgs.).

Office Action dated Oct. 12, 2006 for U.S. Appl. No. 10/691,917 (9 pgs.).

Responsive Amendment dated Jul. 14, 2006 for U.S. Appl. No. 10/691,917 (21 pgs.).

Office Action dated Feb. 28, 2006 for U.S. Appl. No. 10/691,917 (9 pgs.).

Office Action dated Jul. 23, 2008 for U.S. Appl. No. 11/414,625 (15 pgs.).

Responsive Amendment dated Oct. 21, 2008 for U.S. Appl. No. 11/414,625 (15 pgs.).

Office Action dated Jun. 17, 2009 for U.S. Appl. No. 10/691,917 (5 pgs.).

Response dated Sep. 17, 2009 for U.S. Appl. No. 10/691,917 (6 pgs.).

Office Action dated Aug. 21, 2009 for U.S. Appl. No. 11/414,625 (9 pgs.).

Office Action dated Jun. 24, 2010 for U.S. Appl. No. 11/414,625 (4 pgs.).

Responsive Amendment dated Jul. 9, 2010 for U.S. Appl. No. 11/414,625 (14 pgs.).

Supplemental Amendment dated Jul. 28, 2010 for U.S. Appl. No. 11/414,625 (12 pgs.).

Office Action dated May 21, 2010 for U.S. Appl. No. 11/607,454 (7 pgs.).

Responsive Amendment dated Aug. 23, 2010 for U.S. Appl. No. 11/607,454 (12 pgs.).

Notification of Transmittal of the International Search Report and the Written Opinion dated Apr. 20, 2007 for application No. PCT/US2006/046087, filed Dec. 1, 2006 (10 pgs.).

Notification of Transmittal of the International Search Report and the Written Opinion dated Apr. 19, 2007 for application No. PCT/US2006/046061, filed Dec. 1, 2006 (12 pgs.).

Responsive Amendment dated May 28, 2009 for U.S. Appl. No. 11/414,625 (21 pgs.).

U.S. Appl. No. 12/966,827, filed Dec. 13, 2010, entitled: Closed-Loop Therapy Adjustment.

U.S. Appl. No. 13/154,303, filed Jun. 6, 2011, entitled: Closed-Loop Therapy Adjustment.

U.S. Appl. No. 12/433,854, filed Apr. 30, 2009, entitled: Defining Therapy Parameter Values for Posture States.

Response to Office Action dated Jul. 10, 2012, from U.S. Appl. No. 12/966,827, filed Oct. 10, 2012, 11 pp.

Leung et al., "An integrated dual sensor system automatically optimized by target rate histogram," Pacing and Clinical Electrophysiology, vol. 21, No. 8, pp. 1559-1566, Aug. 8, 1998.

(56) References Cited

OTHER PUBLICATIONS

Saoudi et al., "How smart should pacemakers be?," American Journal of Cardiology, vol. 83, No. 5, pp. 180D-186D, Mar. 5, 1999.
Office Action from U.S. Appl. No. 12/966,827, dated Jan. 11, 2013, 8 pp.
Response to Office Action dated Jan. 11, 2013, from U.S. Appl. No. 12/966,827, filed Apr. 11, 2013, 5 pp.
Non-Final Office Action From U.S. Appl. No. 12/966,827, dated Aug. 15, 2013, 9 pp.
Non-Final Office Action from U.S. Appl. No. 13/154,303, dated Aug. 16, 2013, 8 pp.
Office Action from U.S. Appl. No. 12/966,827 dated Dec. 4, 2013, 10 pp.
Office Action from U.S. Appl. No. 13/154,303 dated Dec. 5, 2013, 7 pp.
Response to Office Action dated Aug. 1, 2013, from U.S. Appl. No. 13/764,054, filed Nov. 1, 2013, 15 pp.
Response to Office Action dated Aug. 15, 2013, from U.S. Appl. No. 12/966,827, filed Nov. 15, 2013, 3 pp.
Response to Office Action dated Aug. 16, 2013, from U.S. Appl. No. 13/154,303, filed Nov. 15, 2013, 6 pp.
Final Office Action for U.S. Appl. No. 13/764,054, dated Jan. 31, 2014, 9 pages.
Response to Office Action dated Dec. 5, 2013 from U.S. Appl. No. 13/154,303, filed Mar. 5, 2014, 8 pages.

\* cited by examiner

| Program Table Record | Accelerometer Output | Amplitude (V) | Pulse Width (μs) | Frequency (Hz) | Electrode Configuration |
|---|---|---|---|---|---|
| 1 | [X1, Y1, Z1] | 2.0 | 150 | 10 | 1+ 2- |
| 2 | [X2, Y2, Z2] | 2.5 | 200 | 50 | 1- 2+ |
| 3 | [X3, Y3, Z3] | 1.0 | 100 | 40 | 3- 2+ |
| 4 | [X4, Y4, Z4] | 6.6 | 100 | 40 | 1- 3+ |
| 5 | [X5, Y5, Z5] | 8.3 | 100 | 35 | 8- 6+ |

CLOSED-LOOP THERAPY ADJUSTMENT

This application is a continuation of U.S. application Ser. No. 11/607,426, filed Dec. 1, 2006, which claims the benefit of U.S. Provisional Application Ser. No. 60/742,044, filed Dec. 2, 2005. The entire content of each of these Applications is incorporated herein by reference.

TECHNICAL FIELD

The invention relates to medical devices and, more particularly, medical devices that deliver therapy.

BACKGROUND

A variety of types of medical devices are used for chronic, e.g., long-term, provision of therapy to patients. As examples, pulse generators are used for chronic provision of cardiac pacing and neurostimulation therapies, and pumps are used for chronic delivery of therapeutic agents, such as drugs. Typically, such devices provide therapy continuously or periodically according to parameters, e.g., a program comprising respective values for each of a plurality of parameters, specified by a clinician.

In some cases, the patient is allowed to activate and/or modify the therapy. For example, the symptoms, e.g., the intensity of pain, of patients who receive spinal cord stimulation (SCS) therapy may vary over time based on the activity level or posture of the patient, the specific activity undertaken by the patient, or the like. For this reason, a patient who receives SCS therapy from an implantable medical device (IMD), e.g., an implantable pulse generator, is often given a patient programming device that communicates with his IMD via device telemetry, and allows the patient to activate the neurostimulation and/or adjust the intensity of the delivered neurostimulation.

SUMMARY

In general, the invention is directed to techniques for detecting a value of a sensed patient parameter, and automatically delivering therapy to a patient according to therapy information previously associated with the detected value. More particularly, the techniques include receiving a therapy adjustment from the patient or other user and, in response to the adjustment, associating a sensed value of a patient parameter with therapy information determined based on the adjustment. The association may be automatic, or after user confirmation. Therapy may then be delivered according to the associated therapy information whenever the parameter value is subsequently detected. In this manner, as an example, a processor of a medical device that delivers therapy to the patient, or of some other component of a system including such a medical device, may "learn" to automatically adjust the therapy in the manner desired by the patient as the sensed parameter of the patient changes.

The processor may maintain a data structure, such as a program table. Each individual "record" within the data structure may include therapy information associated with a respective parameter value. When the processor detects a parameter value, the processor may determine whether any of the records of the data structure include the parameter value. If a record includes the parameter value, the processor may control delivery of stimulation by the medical device according to the therapy information associated with the parameter value in the record. Additionally, when the processor receives a therapy adjustment from the patient or other user, and associates a patient parameter value with therapy information, the processor may determine whether any existing records already include the parameter value. The processor may modify an existing record to include the therapy information, or create a new record that includes the therapy information. The medical device may deliver stimulation, such as spinal cord stimulation or some other neurostimulation, and therapy information may include stimulation parameters, such as respective values for pulse amplitude, width and rate, as well as an electrode configuration.

In some embodiments, a plurality of parameters of the patient is sensed. In such embodiments, therapy information may be associated with respective values for each of the plurality of parameters in response to receipt of a therapy adjustment from the patient. In such embodiments, subsequently detection may involve the detection of the particular respective values in combination. Exemplary patient parameters that may be sensed for performance of the techniques of the invention include posture, activity, heart rate, temperature, respiration rate, and pH.

A patient may manually change or adjust stimulation parameters to customize the therapy as needed. While manual adjustment may ultimately result in efficacious therapy, it does so only after the time and patient effort intrinsic in such adjustment. Embodiments of the invention may be able to more quickly and easily provide a patient with efficacious therapy through "learned" associations of sensed patient parameter values with therapy information. For example, a medical device according to the invention may learn to automatically adjust therapy in the manner desired by the patient based on such associations. After a sufficient period of therapy, the patient may no longer need to manually adjust the therapy because the medical device has learned to use values of one or more sensed patient parameters to anticipate any adjustments.

In one embodiment, the disclosure provides a method that comprises receiving a therapy adjustment and a subsequent confirmation from a user, determining therapy information based on the therapy adjustment, associating the therapy information with a value of a sensed parameter of a patient in response to the confirmation, subsequently detecting the value of the sensed parameter; and automatically delivering therapy to the patient according to the therapy information associated with the value in response to the detection.

In another embodiment, the disclosure provides a system comprising a medical device that delivers a therapy to a patient, a sensor that senses a parameter of the patient, a user interface, and a processor. The processor receives a therapy adjustment and subsequent confirmation from a user via the user interface, determines therapy information based on the therapy adjustment, associates a value of the sensed parameter detected via the sensor with the therapy information in response to the confirmation, subsequently detects the value via the sensor, and automatically controls the medical device to deliver therapy to the patient according to the therapy information associated with the value in response to the detection.

In another embodiment, the disclosure provides a system comprising means for sensing a parameter of a patient, means for receiving a therapy adjustment and a subsequent confirmation from a user, means for determining therapy information based on the therapy adjustment, means for associating the therapy information with a value of a sensed parameter of a patient in response to the confirmation, means for subsequently detecting the value of the sensed parameter, and means for automatically delivering therapy to the patient according to the therapy information associated with the value in response to the detection.

Further, in other embodiments, the disclosure provides computer-readable media comprising instructions that cause a programmable processor to perform any of the methods or techniques described herein.

In various embodiments, the invention may provide one or more advantages. For example, the patient may rarely need to manually enter an adjustment to the therapy after a medical device or other component of a system according to the invention learns to automatically adjust the therapy based on sensed patient parameter values. In addition, to the extent that the symptoms of the patient change over time, the patient may further adjust the therapy, systems according to the invention may learn to deliver therapy according to these adjustments, e.g., by modifying existing records stored in a program table.

The details of one or more embodiments of the invention are set forth in the accompanying drawings and the description below. Other features, objects, and advantages of the invention will be apparent from the description and drawings, and from the claims.

DETAILED DESCRIPTION

Electrical stimulation is one example of a therapy that may be delivered in a closed-loop manner according to the present invention. Electrical stimulation may be, for example, used to treat patients that suffer from chronic back pain, leg pain, or other pain that cannot be treated through other methods. As a patient changes posture, the stimulation may need to be adjusted in order to maintain efficacy. The patient may use a programmer to manually change one or more stimulation parameters, e.g., amplitude, to adjust the therapy in response to the posture change. Alternatively, the patient may select a new stimulation program, the program including new respective values for each of the stimulation parameters, to adjust the therapy.

While manual adjustment of stimulation may be effective, the patient is burdened by the need to adjust the therapy throughout a daily routine. According to some embodiments of the invention, a medical device, e.g., an implantable medical device (IMD), includes or is coupled to a sensor that senses a patient parameter, and delivers closed-loop therapy based on values of the patient parameter. The IMD "learns" to provide closed-loop therapy based on therapy adjustments made by the patient. In particular, the IMD associates patient parameter values with therapy information in response to therapy adjustments, and then automatically delivers therapy according to therapy information associated with parameter values. The patient may rarely need to manually enter an adjustment to the therapy after a medical device or other component of a system according to the invention learns to automatically adjust the therapy based on sensed patient parameter values.

For example, the IMD may store a table or other data structure that contains records, in which each record contains therapy information associated with a respective value of a patient parameter. The IMD may automatically update the table in response to a therapy adjustment from the patient, or may update the table after receiving confirmation that the adjusted therapy is desired. The IMD may update the program table after every adjustment input from the patient, after a complete therapy adjustment that includes a number of inputs, or periodically during therapy. While spinal cord stimulation (SCS) is described herein, the invention may be applicable to any type of stimulation therapy. Further, the invention may be applicable to other non-stimulation therapies, such as delivery of a therapeutic agent, e.g., a drug.

Figure 1:
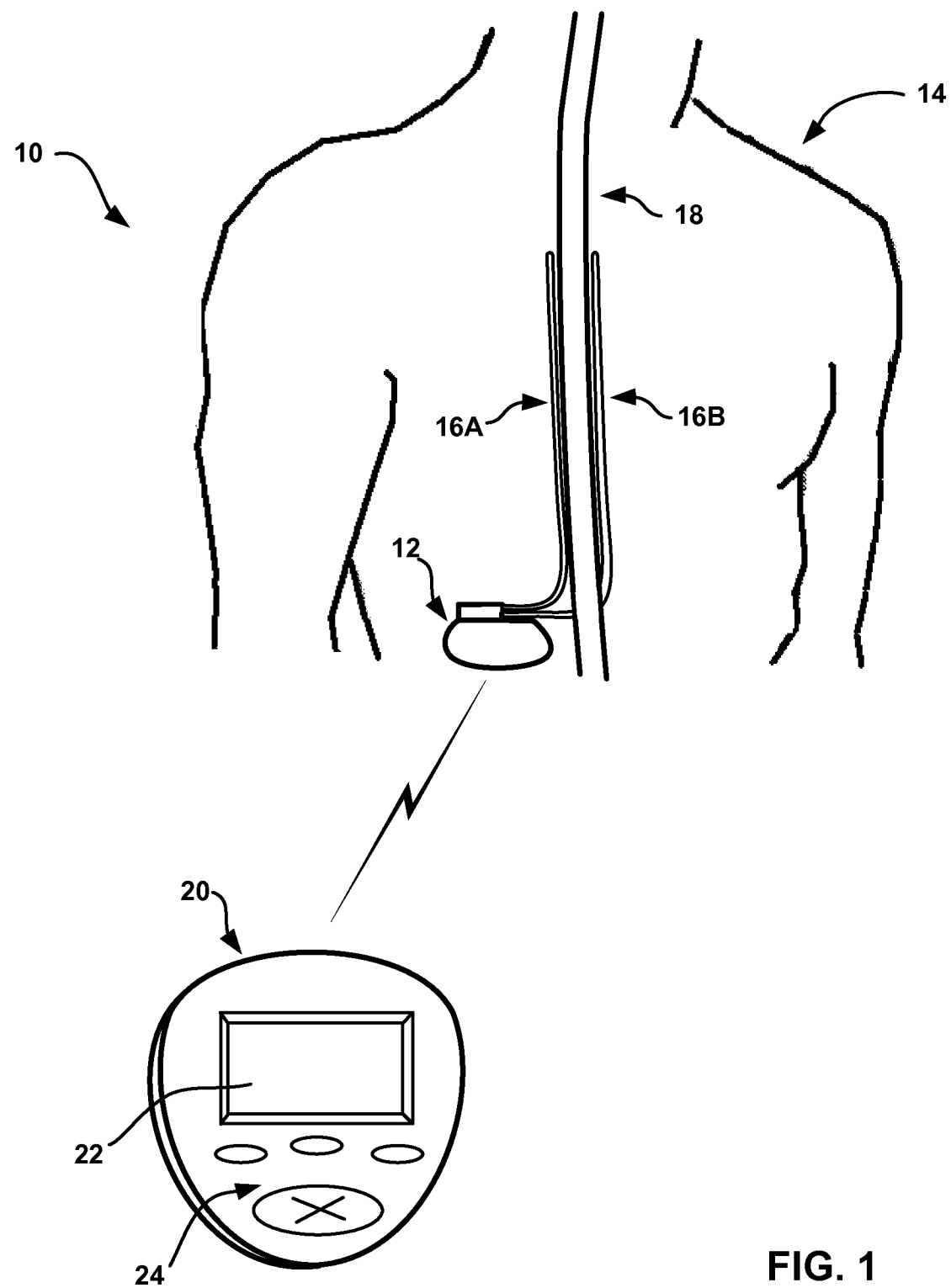
FIG. 1 is a conceptual diagram illustrating an example system that facilitates closed-loop therapy adjustment according to the invention.

FIG. 1 is a conceptual diagram illustrating an example system 10 that facilitates closed-loop therapy adjustment according to the invention. In the illustrated example, system 10 includes an IMD 12, which is implanted within a patient 14, and delivers neurostimulation therapy to patient 14. In exemplary embodiments, IMD 12 takes the form of an implantable pulse generator, and delivers neurostimulation therapy to patient 14 in the form of electrical pulses.

IMD 12 delivers neurostimulation therapy to patient 14 via leads 16A and 16B (collectively "leads 16"). Leads 16 may, as shown in FIG. 1, be implanted proximate to the spinal cord 18 of patient 14, and IMD 12 may deliver SCS therapy to patient 14 in order to, for example, reduce pain experienced by patient 14. However, the invention is not limited to the configuration of leads 16 shown in FIG. 1 or the delivery of SCS therapy. For example, one or more leads 16 may extend from IMD 12 to the brain (not shown) of patient 14, and IMD 12 may deliver deep brain stimulation (DBS) therapy to patient 14 to, for example, treat tremor, Parkinson's disease, or epilepsy. As further examples, one or more leads 16 may be implanted proximate to the pelvic nerves (not shown), stomach (not shown), or sexual organs (not shown) and IMD 12 may deliver neurostimulation therapy to treat incontinence, gastroparesis, or sexual dysfunction.

Further, as discussed above, the invention is not limited to embodiments in which IMD 12 delivers stimulation therapy.

For example, in some embodiments, IMD 12 may additionally or alternatively be coupled to one or more catheters to deliver one or more therapeutic substances to patient 14, e.g., one or more drugs. Additionally, the invention is not limited to implanted devices. Any implantable or external medical device may deliver closed-loop therapy according to the techniques of the invention.

In exemplary embodiments, IMD 12 delivers therapy according to one or more programs. A program includes one or more parameters that define an aspect of the therapy delivered by the medical device according to that program. For example, a program that controls delivery of stimulation by IMD 12 in the form of pulses may define a voltage or current pulse amplitude, a pulse width, a pulse rate, for stimulation pulses delivered by IMD 12 according to that program. Further, each of leads 16 includes electrodes (not shown in FIG. 1), and the parameters for a program that controls delivery of stimulation therapy by IMD 12 may include information identifying which electrodes have been selected for delivery of pulses according to the program, and the polarities of the selected electrodes, i.e., the electrode configuration for the program. Programs that control delivery of other therapies by IMD 12 may include other parameters. For example, a program that controls delivery of a drug or other therapeutic agent may include a titration rate or information controlling the timing of bolus deliveries.

In exemplary embodiments, IMD 12 may also deliver therapy to patient 14 according to therapy information within a record. A plurality of records are stored in a table or other data structure that is continually updated as IMD 12 "learns" associations of therapy information with patient parameter values. Each record includes at least one sensed patient parameter value and associated therapy information. The therapy information may comprise a complete program that IMD 12 uses to deliver therapy, one or more parameter values, or absolute or percentage adjustments for one or more parameters. When IMD 12 detects a value of a patient parameter value, IMD 12 may adjust therapy as indicated by the therapy information in the record for the parameter value, e.g., deliver therapy according to the program in the record, or adjust one or more parameters as indicated by the therapy information in the record.

In the illustrated example, system 10 also includes a programming device 20, which may, as shown in FIG. 1, be a handheld computing device. Programming device 20 allows a user to interact with IMD 12. Programming device 20 may, for example, communicate via wireless communication with IMD 12 using radio-frequency (RF) telemetry techniques, or any other techniques known in the art.

Programming device 20 may, as shown in FIG. 1, include a display 22 and a keypad 24 to allow the user to interact with programming device 20. In some embodiments, display 22 may be a touch screen display, and the user may interact with programming device 20 via display 22. The user may also interact with programming device 20 using peripheral pointing devices, such as a stylus or mouse. Keypad 24 may take the form of an alphanumeric keypad or a reduced set of keys associated with particular functions. In some embodiments, keypad 24 may include an increase amplitude button and a decrease amplitude button to directly adjust stimulation amplitude.

In exemplary embodiments, programming device 20 is a patient programmer used by patient 14 to control the delivery of neurostimulation therapy by IMD 12. Patient 14 may use programming device 20 to activate or deactivate, e.g., start or stop, neurostimulation therapy. Patient 14 may also use programming device 20 to adjust the therapy. For example, a patient may use programming device 20 to select one or more programs from among a plurality of stored programs to be the current programs used by IMD 12 to deliver therapy, e.g., patient 14 may switch from one program to another using programming device 20. The programs may be stored by IMD 12 or patient programmer 20. Further, patient 14 may also use programming device 20 to adjust therapy by adjusting one or more stimulation parameters, e.g., adjust the amplitude, width, or rate of delivered stimulation pulse, for the one or more current programs.

Patient 14 may provide a number of consecutive inputs to adjust the therapy information. These consecutive inputs may be described singly as a "therapy adjustment." Programming device 20 and IMD 12 may treat all consecutive inputs as an adjustment before acting on the changes. Each input may only be separated by a pre-defined time delay, or all inputs may occur within a predefined time period, to treat the inputs as one adjustment.

When patient 14 adjusts one or more stimulation parameters, and/or switches programs, IMD 12 detects a value of a sensed patient parameter, and associates therapy information with the detected value. In some embodiments, IMD 12 stores the associated parameter value and therapy information as a record within a table or other data structure. If an existing record contains the same parameter value, IMD 12 may modify the record to include new therapy information based on the patient adjustment. Otherwise, IMD 12 may add a new record with the associated patient parameter value and therapy information.

In some embodiments, the table or other data structure may be maintained by, and stored in, programming device 20 instead of IMD 12. Accordingly, one or both of IMD 12 and programming device 20 may provide closed-loop adjustment of the therapy delivered by IMD 12 according to the invention. In embodiments in which programming device 20 maintains the data structure, the programming device may receive therapy adjustments from patient 14 via user interface components such as display 22 and keypad 24. In such embodiments, programming device 20 may include sensors that sense the patient parameter, or may receive values of the patient parameter from IMD 12. Programming device 20 may send commands to IMD 12 based on therapy information stored in the data structure to effect closed-loop delivery of therapy.

For ease of description, the provision of closed-loop therapy adjustment will be described hereinafter primarily with reference to embodiments in which IMD 12 provides the closed-loop therapy adjustments. However, it is understood that both of IMD 12 and programming device 20 are medical devices capable of providing closed-loop therapy adjustments according to the invention.

In response to receiving a therapy adjustment from patient 14, e.g., via programming device 20, IMD 12 detects a value of a sensed patient parameter, and associates therapy information with the value. The sensed parameter value may be an activity and/or posture of patient 14, and the therapy information may include the therapy parameters currently used, or adjustments to such parameters made, at the time the sensed patient parameter value was detected. In exemplary embodiments, IMD 12 continually "learns" such associations, e.g., by updating a data structure. Closed-loop delivery of therapy by IMD 12 based on the associations of therapy information with sensed patient parameter values may eventually eliminate the need for patient 14 to manually adjust therapy parameters.

For example, patient 14 may adjust the amplitude of stimulation, which may indicate that the original program was inadequate to treat the patient because of a change of symptoms. The change in symptoms may be correlated with a change in a sensed patient parameter. For example, both of these changes may be due to the patient undertaking an activity or posture, such as running, golfing, taking medication, sleeping, sitting, bending over, transitioning from sitting to standing, or some particular activity or posture related to an occupation of patient 14. IMD 12 may associate therapy information determined based on the received therapy adjustment with a value of a patient parameter, e.g., an activity, activity level, or posture, that is sensed at the time of the therapy adjustment.

In some embodiments, a user other than patient 14 may user programmer 20, or another programming device that may or may not be associated with patient 14, to adjust therapy for patient. The therapy adjustments made by another user may result in updating the table or other data structure with a new or modified association of a therapy information with a patient parameter value.

Further, in some embodiments, IMD 12 may also monitor the sensed patient parameter, and create additional associations between parameter values and existing therapy information, without receiving any therapy adjustment from patient 14. In particular, when the sensed patient parameter value has changed without a therapy adjustment, IMD 12 may automatically associate the parameter value with therapy information determined based on the current, unadjusted therapy parameters. In some embodiments, IMD 12 may only make such an automatic, non-adjustment based association if the sensed patient parameter value has changed by a threshold or "resolution" value, which may be for example an absolute or percentage value.

The resolution value for the sensed patient parameter may control the size and resolution of a data structure that stores associations between values of the patient parameter and therapy information; whether the associations are made based on a therapy adjustment or not. The resolution value may be set by, for example, a manufacturer of IMD 12 or a clinician, and controls difference in the parameter value that IMD 12 identifies as being significant enough to update the data structure. If the resolution value is set to a low value, the data structure may include a greater number of records, each with respective values for the patient parameter. A low resolution value may accordingly provide a finer stimulation control. Alternatively, the resolution value may be set to a higher value to limit the number of records in the data structure, which would also result in less frequent therapy adjustments. In some embodiments, IMD 12 may lower the resolution value if existing records are frequently being modified or overwritten, e.g., in response to frequent therapy adjustments by the patient or other user. This occurrence may indicate that patient 12 or other user needs finer control of adjustments to stimulation therapy.

The sensed patient parameter may be activity, activity level, posture, or a physiological parameter of patient 14. Physiological parameters may include heart rate, electromyography (EMG), an electroencephalogram (EEG), an electrocardiogram (ECG), temperature, respiration rate, or pH. A sensor used to sense such patient parameters may be implanted at a site within patient 14, worn on the exterior of the patient, or located within IMD 12. An example sensor is a 3-axis accelerometer located within IMD 12. Patient parameter values detected by IMD 12 based on the signals generated by such a sensor may correspond to an activity or posture undertaken by patient 14, or a gross level of physical activity, e.g., activity counts based on footfalls or the like.

As an example, IMD 12 may record the output of a 3-axis accelerometer in response to a therapy adjustment, and associate the output with therapy information determined based on the adjustment. The recorded output may be the result of patient 14 being in a prone position, for example. When IMD 12 later detects the same output from the accelerometer, e.g., when patient 14 is again in the prone position, IMD 12 may automatically deliver therapy appropriate for the prone position.

By providing therapy adjustments automatically, IMD 12 may allow patient 14 to avoid having to manually adjust the therapy each time a particular patient parameter value occurs, e.g., each time the patient engages in a particular activity, activity level or posture. Such manual adjustment of stimulation parameters can be tedious, requiring patient 14 to, for example, depress one or more keys of keypad 24 multiple times during the patient activity to maintain adequate symptom control. Instead, according to the invention, patient 14 may eventually need to manually adjust stimulation therapy rarely, if at all, once IMD 12 has compiled a comprehensive program table.

Figure 2:
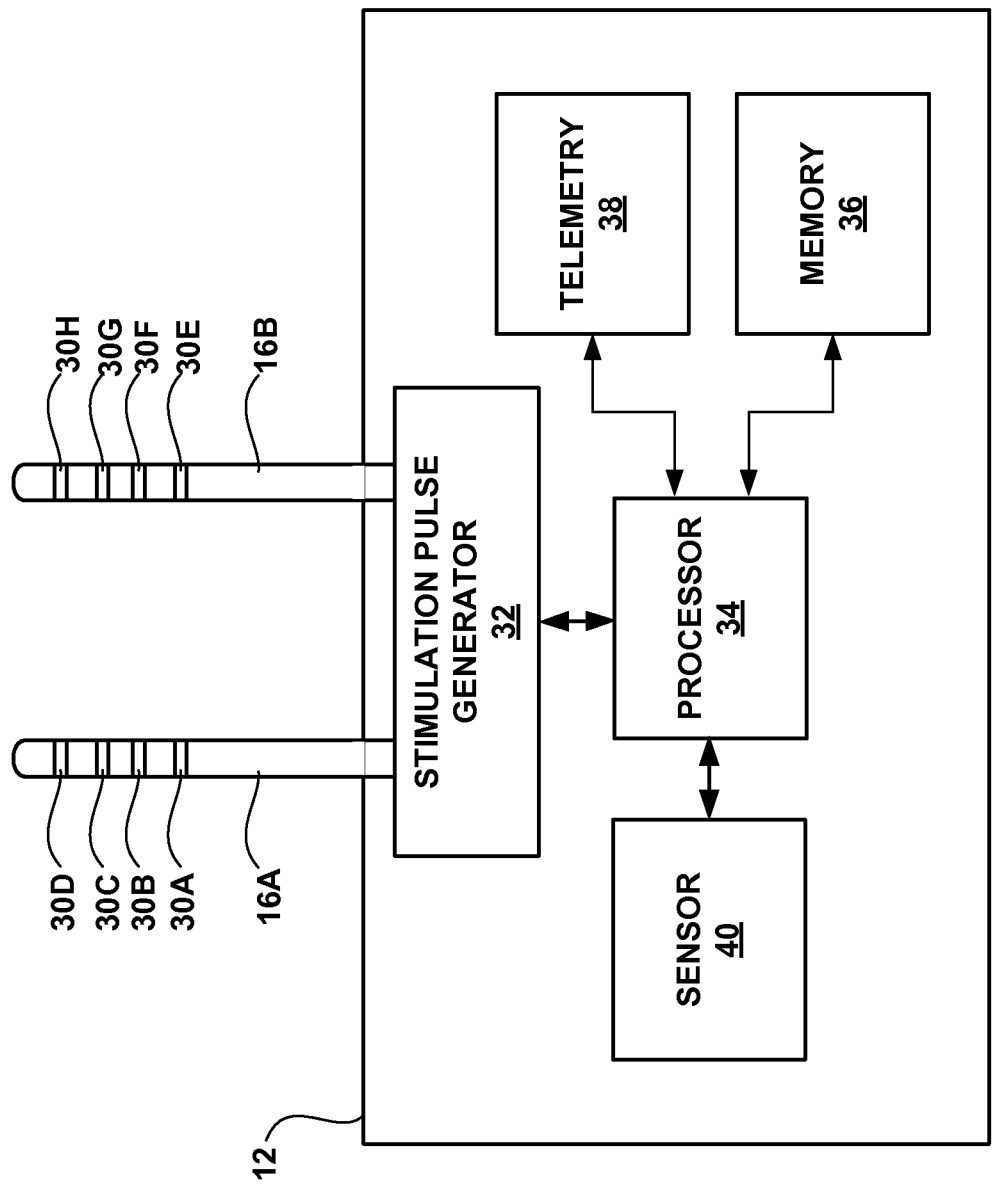
FIG. 2 is a block diagram illustrating an example medical device that delivers therapy and provides closed-loop adjustment of the therapy according to the invention.

FIG. 2 is a block diagram illustrating IMD 12 in greater detail. IMD 12 may deliver neurostimulation therapy via electrodes 30A-D of lead 16A and electrodes 30E-H of lead 16B (collectively "electrodes 30"). Electrodes 30 may be ring electrodes. The configuration, type and number of electrodes 30 illustrated in FIG. 2 are merely exemplary. For example, IMD 12 may only include one lead with eight electrodes on the lead.

Electrodes 30 are electrically coupled to a stimulation pulse generator 32 via leads 16. Stimulation pulse generator 32 may, for example, include an output pulse generator coupled to a power source such as a battery. Stimulation pulse generator 32 may deliver electrical pulses to patient 14 via at least some of electrodes 30 under the control of a processor 34.

Processor 34 may control stimulation pulse generator 32 to deliver neurostimulation therapy according to a selected program. Specifically, processor 34 may control circuit 32 to deliver electrical pulses with the amplitudes and widths, and at the rates specified by the program. Processor 34 may also control stimulation pulse generator 32 to deliver the pulses via a selected subset of electrodes 30 with selected polarities, e.g., a selected electrode configuration, as specified by the program.

Processor 34 may also control stimulation pulse generator 32 to deliver the neurostimulation therapy according to records stored within a table or other data structure, as described above. Processor 34 maintains, e.g., creates and modifies, the table. Specifically, processor 34 may receive a therapy adjustment from a user, such as patient 14, detect a patient parameter value, and associate therapy information with the patient parameter value by creating or modifying a record within the data structure, as described above.

Processor 34 may subsequently detect previously detected patient parameter values, and control stimulation pulse generator 32 to deliver therapy via at least some of electrodes 30 as indicated by the associated therapy information. For example, processor 34 may control stimulation pulse generator 32 to deliver stimulation pulses with the amplitude, width, rate, and/or electrode configuration indicated by the therapy information, or, in some embodiments, may control stimulation pulse generator 32 to adjust the amplitude, width, and/or rate over time as indicated by the therapy information.

IMD 12 also includes a telemetry circuit 38 that allows processor 34 to communicate with programming device 20. Processor 34 may receive program selections, therapy parameter adjustments, or other therapy adjustments, as well as commands to initiate or terminate stimulation, from a user, e.g., patient 14, using programming device 20 via telemetry circuit 38. In some embodiments, as will be described in greater detail below, processor 34 also communicates with a clinician programmer to provide diagnostic information stored in memory 36 to a clinician via telemetry circuit 38. The clinician programmer may operate similarly to programmer 20, but the clinician programmer may be more fully featured, e.g., provide greater control of or interaction with IMD 12, than programming device 20. Telemetry circuit 38 may correspond to any telemetry circuit known in the implantable medical device arts.

In exemplary embodiments, as described above, IMD 12 includes a sensor 40 that senses a patient parameter, and processor 34 detects values of the patient parameter based on the signal generated by sensor 40 as a function of the patient parameter. Sensor 40 may be a sensor that generates an output based on activity, activity level, posture, and/or one or more physiological parameters of patient 14, as discussed above. In exemplary embodiments, sensor 40 is a 3-axis accelerometer, such as a piezoelectric and/or micro-electro-mechanical accelerometer. In other embodiments, a single axis accelerometer may be employed, or multiple single axis accelerometers may be used in place of one 3-axis accelerometer.

In some embodiments, processor 34 processes the analog output of sensor 40 to determine digital activity and/or posture information. For example, where sensor 40 comprises a piezoelectric accelerometer, processor 34 may process the raw signal provided by sensor 40 to determine activity counts. In some embodiments, IMD 12 includes multiple sensors oriented along various axes, or sensor 40 comprises a single multi-axis, e.g., three-axis, accelerometer. In such embodiments, processor 34 may process the signals provided by the one or more sensors 40 to determine velocity of motion information for each axis.

Although illustrated in FIG. 2 as including a single sensor 40, systems according to the invention may include any number of sensors 40. In exemplary embodiments, the one or more sensors 40 are housed within a housing (not shown) of IMD 12. However, the invention is not so limited. In some embodiments, one or more sensors 40 are coupled to IMD 12 via additional leads 16 (not shown). Such sensors may be located anywhere within patient 14. In some embodiments, IMD 12 may be coupled to multiple accelerometer sensors 40 located at various positions within patient 14 or on the external surface of patient 14, and processor 34 may receive more detailed information about the posture of and activity undertaken by patient 14. For example, accelerometer sensors 40 may be located within the torso and at a position within a limb, e.g. a leg, of patient 14.

In some embodiments, one or more sensors 40 may communicate wirelessly with IMD 12 instead of requiring a lead to communicate with the IMD. For example, sensors 40 located external to patient 12 may communicate wirelessly with processor 34, either directly or via programming device 20. In some embodiments, one or more sensors 40 may be included as part of or coupled to programming device 20.

Moreover, the invention is not limited to embodiments where sensors 40 are accelerometers. In some embodiments, one or more sensors 40 may take the form of, for example, a thermistor, a pressure transducer, or electrodes to detect thoracic impedance or an electrogram. Such sensors 40 may be appropriately positioned within patient 14, or on an external surface of the patient, to allow processor 34 to measure a physiological parameter of patient 14, such as a skin temperature, an arterial or intracardiac pressure, a respiration rate, a heart rate, or a Q-T interval of patient 14.

Processor 34 may include a microprocessor, a controller, a digital signal processor (DSP), an application specific integrated circuit (ASIC), a field-programmable gate array (FPGA), discrete logic circuitry, or the like. IMD 12 also includes a memory 36, which may include program instructions that, when executed by processor 34, cause IMD 12 to perform the functions ascribed to IMD 12 herein. Memory 36 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like.

Figure 3:
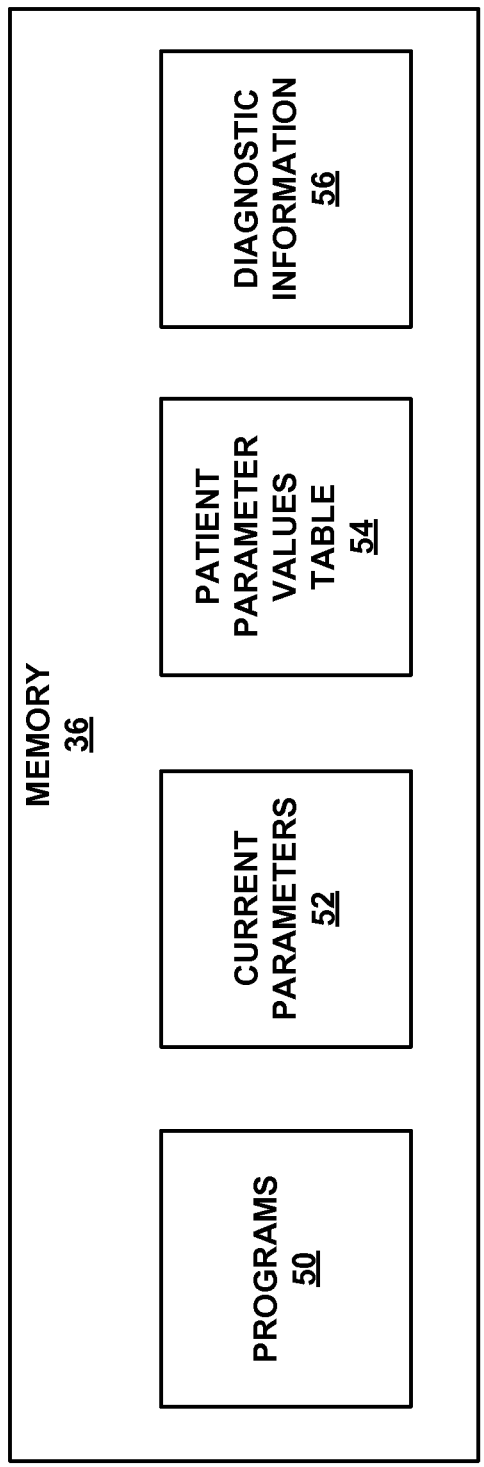
FIG. 3 is a block diagram illustrating an example configuration of a memory of the medical device of FIG. 2.

FIG. 3 is a block diagram illustrating an exemplary configuration of memory 36 of IMD 12. As illustrated in FIG. 3, memory 36 stores programs 50, one or more of which processor 34 (FIG. 2) may select to control delivery of stimulation by pulse generator 32 (FIG. 2), as described above. Each of the programs includes respective values for a plurality of therapy parameters, such as pulse amplitude, pulse width, pulse rate, and electrode configuration, as described above. Processor 34 may select one or more programs based on input or commands received from patient 14 via programming device 20 and telemetry circuit 38. Programs 50 may have been generated using a clinician programmer, e.g., during an initial or follow-up programming session, and received by processor 34 from the clinician programmer via telemetry circuitry 38. In other embodiments, programming device 20 stores programs 50, and processor 34 receives selected programs from programming device 20 via telemetry circuit 38.

In some embodiments, memory 36 also stores an indication of the current therapy parameters 52 used by processor 34 to control delivery of stimulation by stimulation pulse generator 32. Current therapy parameters 52 may be the one or more selected programs, or may reflect modifications to one or more therapy parameters of the one or more programs based on patient adjustment. Further, processor 34 may determine current therapy parameters 52 based on therapy information associated with a detected value of a sensed patient parameter, as described herein.

As described above, patient parameter values table 54 comprises a plurality of records that each include a respective value of a patient parameter and associated therapy information. When therapy is initiated, table 54 may be empty. As therapy progresses, processor 34 creates records, by associating therapy information with patient parameter values, and stores them table 54. If a therapy adjustment causes processor 34 to identify a sensed patient parameter value that is substantially identical to a patient parameter value for an existing record, processor 34 modifies existing record based on new therapy information in order to keep updated therapy information available for stimulation therapy. In this manner, IMD 12 is capable of adapting to changes in patient 14 physiology during the therapy.

Processor 34 may also collect diagnostic information 56 and store diagnostic information 56 within memory 36 for future retrieval by a clinician. Diagnostic information 56 may, for example, include selected recordings of the output of sensor 40 and/or of therapy changes made by patient 14. In exemplary embodiments, diagnostic information 56 includes information identifying the time at which patient sensor outputs occurred, either during operation in a learning mode or as subsequently detected by processor 34. Diagnostic information 56 may include other information or activities indicated by patient 14 using programming device 20, such as changes in symptoms, taking medication, or other activities undertaken by patient 14. A clinician programming device (not shown in FIGS.) may present diagnostic information 56 to a clinician in a variety of forms, such as timing diagrams, or a graph resulting from statistical analysis of diagnostic information 56, e.g., a bar graph. Diagnostic information 56 may also include calibration routines for each sensor 40 and malfunction algorithms to identify stimulation dysfunctions.

Figure 4:
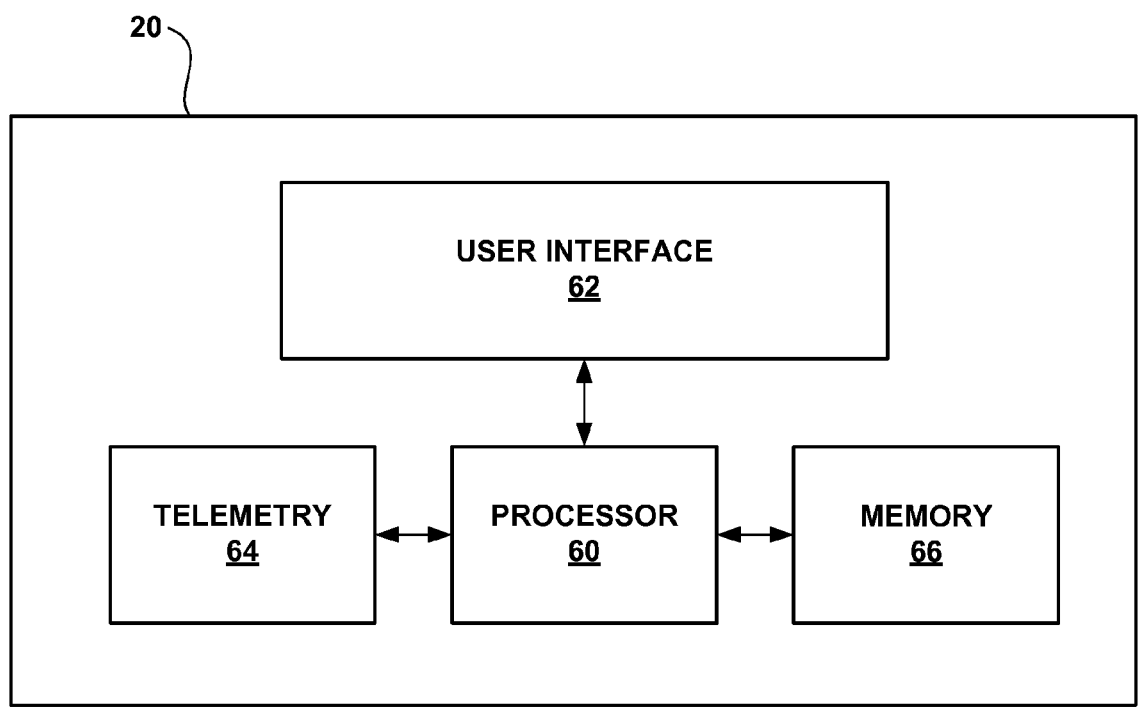
FIG. 4 is a block diagram illustrating an example external programmer that allows a patient to communicate with the medical device of FIG. 2.

FIG. 4 is a block diagram further illustrating programming device 20. As indicated above, in exemplary embodiments programming device 20 takes the form of a patient programming device used by patient 14 to control delivery of therapy by IMD 12. Patient 14 may interact with a processor 60 via a user interface 62 in order to control delivery of neurostimulation therapy, e.g., provide patient therapy adjustments, as described herein. User interface 62 may include display 22 and keypad 24, and may also include a touch screen or peripheral pointing devices as described above. Keypad 24 may include an increase amplitude button and a decrease amplitude button. Processor 60 may also provide a graphical user interface (GUI) to facilitate interaction with patient 14. Processor 60 may include a microprocessor, a controller, a DSP, an ASIC, an FPGA, discrete logic circuitry, or the like.

Programming device 20 also includes a telemetry circuit 64 that allows processor 60 to communicate with IMD 12. In exemplary embodiments, processor 60 communicates commands, indications, and therapy adjustments made by patient 14 via user interface 62 to IMD 12 via telemetry circuit 64. Telemetry circuit 64 may correspond to any telemetry circuit known in the implantable medical device arts.

Programming device also includes a memory 66. In some embodiments, memory 66, rather than memory 36 of IMD 12, may store programs 50 and table 54 to control delivery of neurostimulation therapy. Memory 66 may also include program instructions that, when executed by processor 60, cause programming device 20 to perform the functions ascribed to programming device 20 herein. Memory 66 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Figure 5:
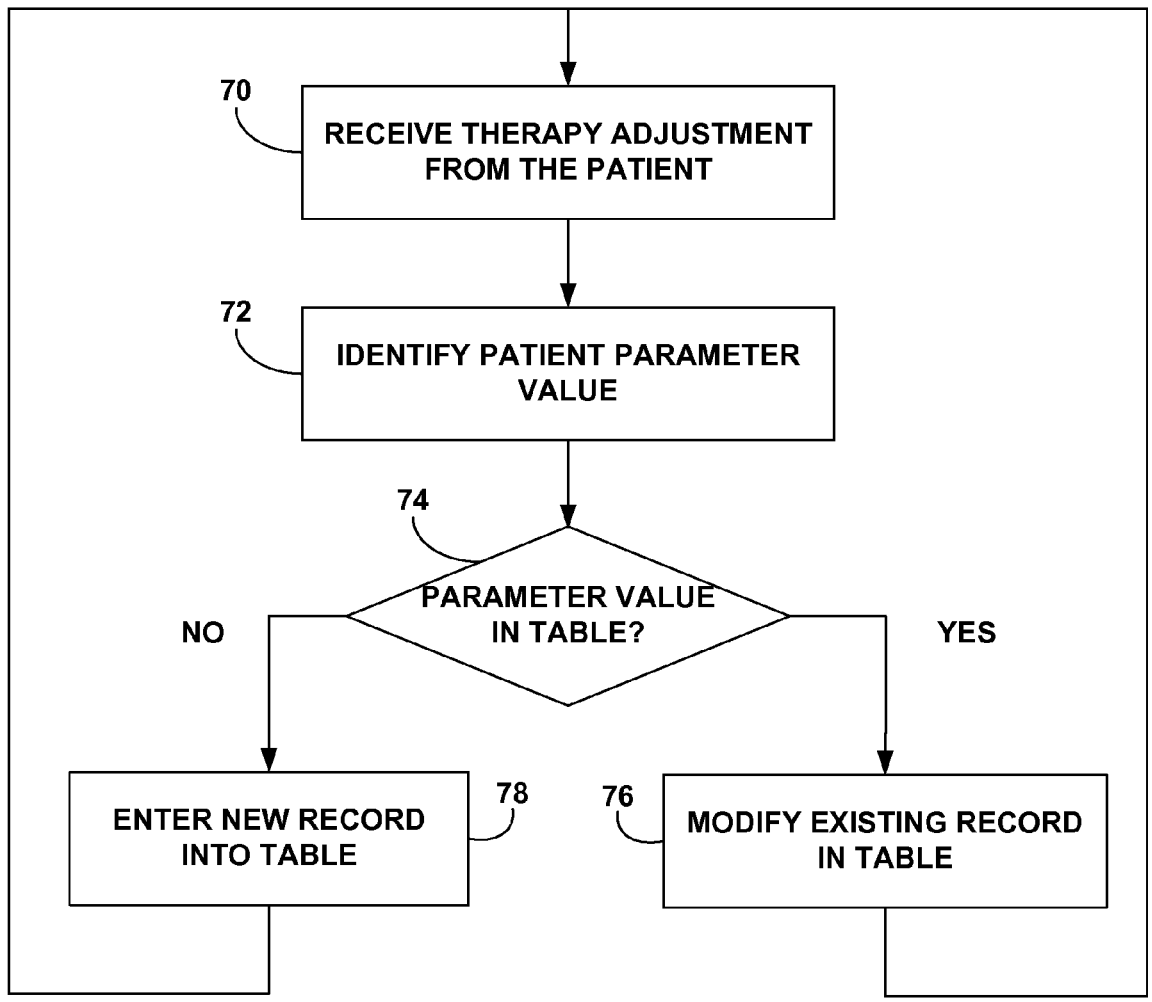
FIG. 5 is a flow diagram illustrating an example technique for automatically associating therapy information with patient parameter values in response to therapy adjustments.

FIG. 5 is a flow diagram illustrating an example technique for automatically associating therapy information with patient parameter values in response to patient therapy adjustments. More particularly, FIG. 5 illustrates an example technique for updating a program table following therapy adjustments by patient 14. The illustrated technique may be performed by a medical device, such as IMD 12, and will be described with reference to IMD 12 and system 10.

During therapy, processor 34 of IMD 12 receives a therapy adjustment from patient 14 via programmer 20, e.g., an amplitude adjustment (70). Processor 34 determines therapy information, such as the amount or percentage of the amplitude adjustment, the adjusted value of the amplitude, or respective values for a plurality of therapy parameters including the adjusted amplitude value, based on the therapy adjustment. Processor 34 also identifies a current value of a sensed patient parameter of patient 14, such as posture or activity, based on a signal generated by sensor 40 (72).

Processor 34 determines whether any of the records in table 54 already include or encompass the identified patient parameter value (74). If the patient parameter value is already in an existing record of table 54, processor 34 modifies the existing record based on, e.g., to include, the newly determined therapy information (76). Otherwise, processor 34 may enter a new record including the identified patient parameter value and the determined therapy information into the table 54 (78). The determination of whether a value of the sensed patient parameter is included in or encompassed by a record already in table 54, e.g., whether the value is substantially equivalent to an existing value, may depend on the resolution value for the sensed parameter, which was discussed above with reference to FIG. 1.

In some cases, the therapy adjustment received from patient 14 may be one or more inputs or a command that stops delivery of therapy. Such an adjustment indicates that the current therapy parameter values 52, whether they were determined based on a program 50 or therapy information from table 54, were inappropriate for the current condition of patient 14. The current condition of the patient is reflected by the current value of a sensed patient parameter. As an example, the patient may stop therapy if it becomes too intense when a particular posture is assumed.

In response to such a therapy adjustment, processor 34 may remove any current association between the current value of the sensed patient parameter and therapy information, e.g., delete any record in table 54 for the current value of the sensed patient parameter. In this manner, next time patient 14 assumes a problematic posture or activity, no change in therapy from whatever therapy is currently being delivered will occur. However, whatever is being delivered may also cause patient 14 to experience discomfort. Accordingly, processor 34 may create a new record, or modify an existing record, such that a relatively innocuous, predetermined therapy program is associated with the patient parameter value that indicates the problematic condition, e.g., posture or activity, of the patient.

Alternatively, processor 34 or programming device 20 may request patient 14 to assume the activity or posture associated with the therapy shutdown, and manually find therapy parameters that provide comfortable and efficacious therapy. In this case, processor 34 or the programming device may provide some guidance or direction to patient 14 to assist in quickly determining therapy parameters that are effective. Once such parameters are found, IMD 12 may create a record in table 54 that associates the previously problematic sensed patient parameter value with the therapy information chosen by patient 14.

Figure 6:
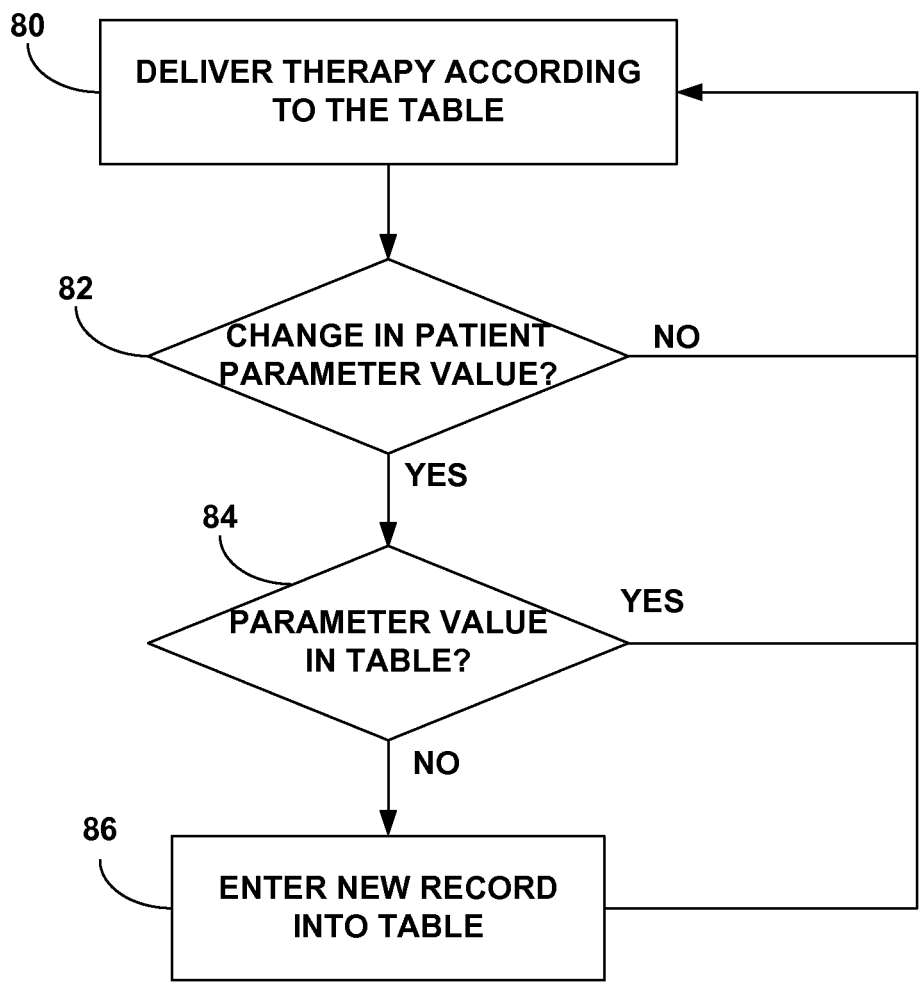
FIG. 6 is a flow diagram illustrating an example technique for delivering stimulation according to existing associations of therapy information and parameter values, and automatically associating existing therapy information with additional patient parameter values.

FIG. 6 is a flow diagram illustrating an example technique for delivering stimulation according to existing associations of therapy information and parameter values, and also automatically associating existing therapy information with additional patient parameter values. The illustrated technique may be performed by a medical device, such as IMD 12, and will be described with reference to IMD 12 and system 10. As shown in FIG. 6, processor 34 of IMD 12 controls pulse generator 32 to deliver therapy according to the therapy information stored in table 54 (80). For example, processor 34 may adjust therapy parameters or change therapy programs as indicated by therapy information stored in records of table 54. Processor 34 accesses different records, and thus different therapy information, based on detected values of a sensed patient parameter.

If processor 34 detects a change in the patient parameter value (82), the processor may determine whether the parameter value is already in the table (84). As discussed above, this determination may depend on a resolution value for the sensed patient parameter. If the detected patient parameter value is already in table 54, processor 34 may control generator 32 to deliver therapy according to the table, e.g., according to the therapy information associated with the detected patient parameter value in the table (80). This may include adjusting one or more parameters or changing a program. If the detected patient parameter value is not already in table 54, processor 34 may enter a new record in table 54 for the value, which associates the detected patient parameter value with the current therapy parameter values 52 (86). In this manner, processor 34 may more quickly populate table 54 with therapy information for various values of the sensed patient parameter than would be possible if generation of new records was limited to being responsive therapy adjustments from by the patient.

In some embodiments, processor 34 may wait a predetermined time after the sensed patient parameter value changes before storing a new record. Since the output of sensor 40 may change rapidly, recording a new record for each small change in sensor output may not be necessary or even possible without slowing down the performance of processor 34. Processor 34 may wait for 10 seconds, for example, in order to let the sensor output stabilize before generating a new record.

Figure 7:
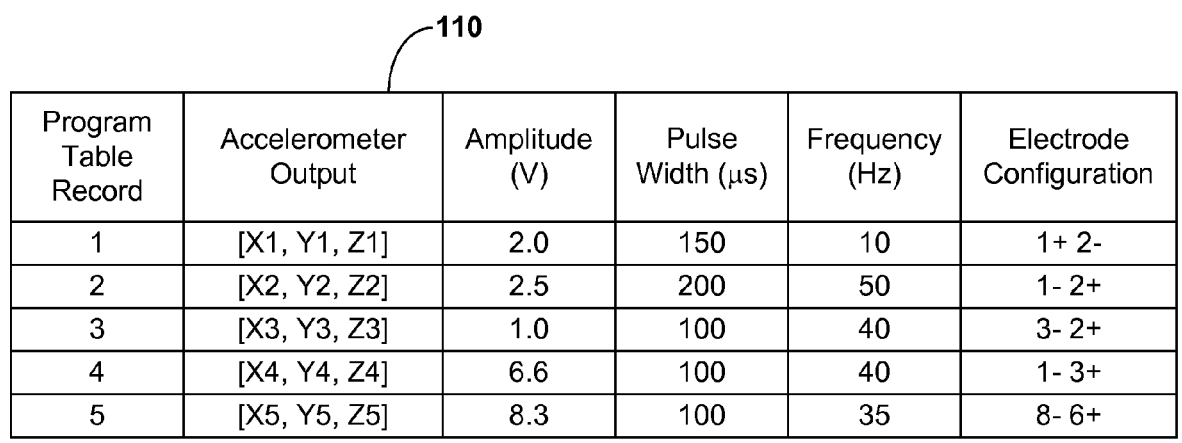
FIG. 7 is a chart illustrating an example patient parameter values table that may be used for closed-loop adjustment of therapy.

FIG. 7 is a chart illustrating an example patient parameter value table that may be used for closed-loop adjustment of therapy. Table 110 may correspond to table 54 stored in memory 36 of IMD 12. As shown in FIG. 7, table 110 includes a plurality of records. Each record contains an accelerometer output, which is an example of a value of a sensed patient parameter, as well as an amplitude, a pulse width, a pulse frequency, and an electrode configuration, which are values for example therapy parameters. Processor 34 may search table 110 based on a currently-detected accelerometer output in order to match therapy to the current condition, e.g., posture, of patient 14.

The accelerometer output is from a 3-axis accelerometer. A measured acceleration in each direction creates a vector acceleration. Therefore, each accelerometer output includes an X variable, a Y variable, and a Z variable. If one of the three variables is different between an existing record and a new record, processor 34 may enter the new record into program table 110. The value of the accelerometer may be a raw value or a calibrated value equal to the actual acceleration. The resolution value may be equal to the maximum range of each acceleration component divided by a pre-set size. For example, the maximum range may be 10 volts, and the pre-set size may be 100. Therefore, the resolution value for each component is 0.1 volts. In some embodiments, each component of the acceleration value may have a different resolution value.

With respect to the therapy information, the amplitude is in volts, the pulse width is in microseconds (µs), the pulse frequency is in Hertz (Hz), and the electrode configuration determines the electrodes and polarity used for delivery of stimulation according to the record. The amplitude of program table 110 is the voltage amplitude, but other embodiments may use a current amplitude. In the illustrated example, each record includes a complete set of therapy parameters, e.g., a complete program, as therapy information. In other embodiments, each record may include one or more individual parameter values, or information characterizing an adjustment to one or more parameter values.

Figure 8:
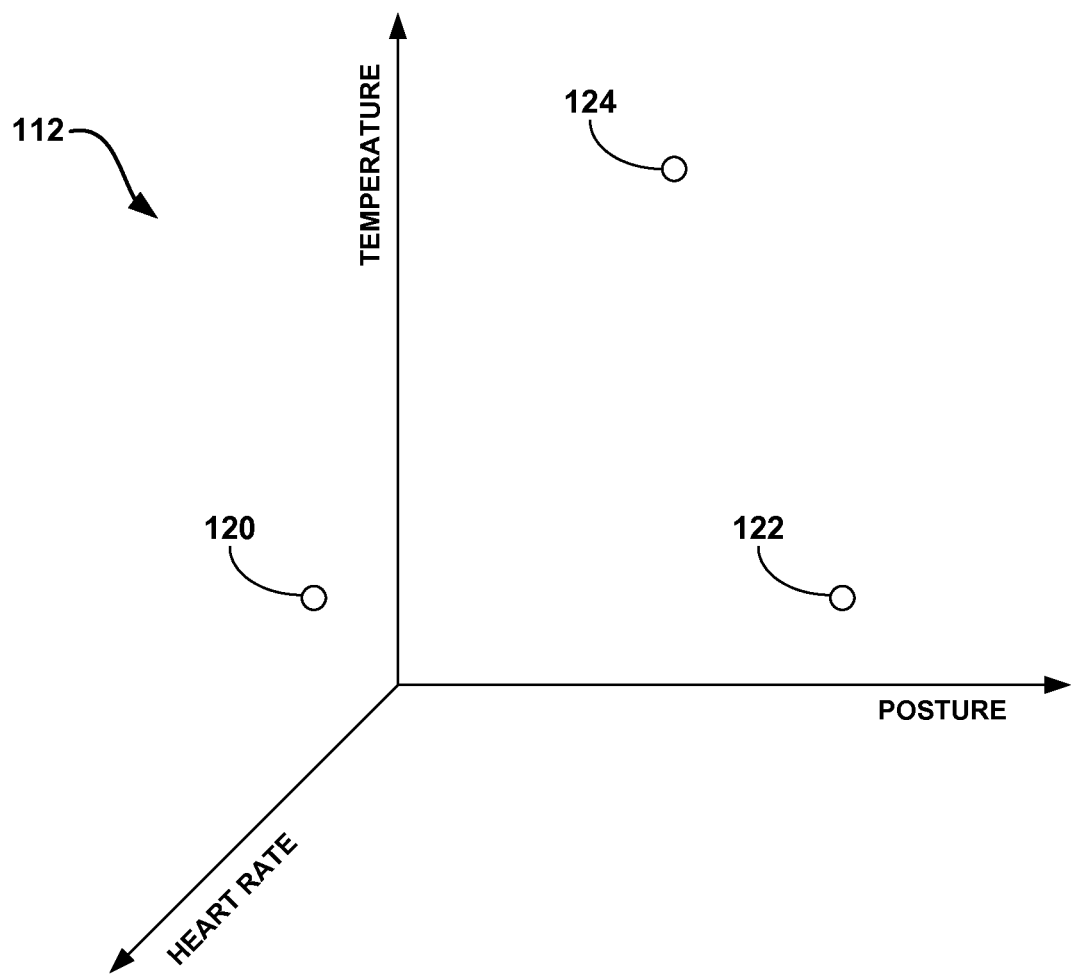
FIG. 8 is a diagram illustrating an example data structure and method for providing closed-loop therapy according to the invention based on multiple sensed patient parameters.

FIG. 8 is a diagram illustrating an example data structure and method for providing closed-loop therapy according to the invention based on multiple sensed patient parameters. In some embodiments, each record of table 54 may include respective values for each of a plurality of sensed patient parameters. Processor 34 may deliver therapy according to therapy information within a record in response to detecting the respective parameter values for the record in combination.

FIG. 8 illustrates a matrix 112, which may correspond to such a table. Records with respective therapy information associated with respective values for each of a plurality of sensed patient parameters may be considered to reside at one of points 120, 122 and 124 within a multi-dimensional patient parameter space. Patient 14 temperature, posture, and heart rate are the three exemplary parameters of three-dimensional matrix 112. Matrix 112 may contain numerous records at various "locations" throughout the parameter space represented by matrix, each record with a respective combination of values for a plurality of sensed patient parameters, which is associated with respective therapy information.

Figure 9:
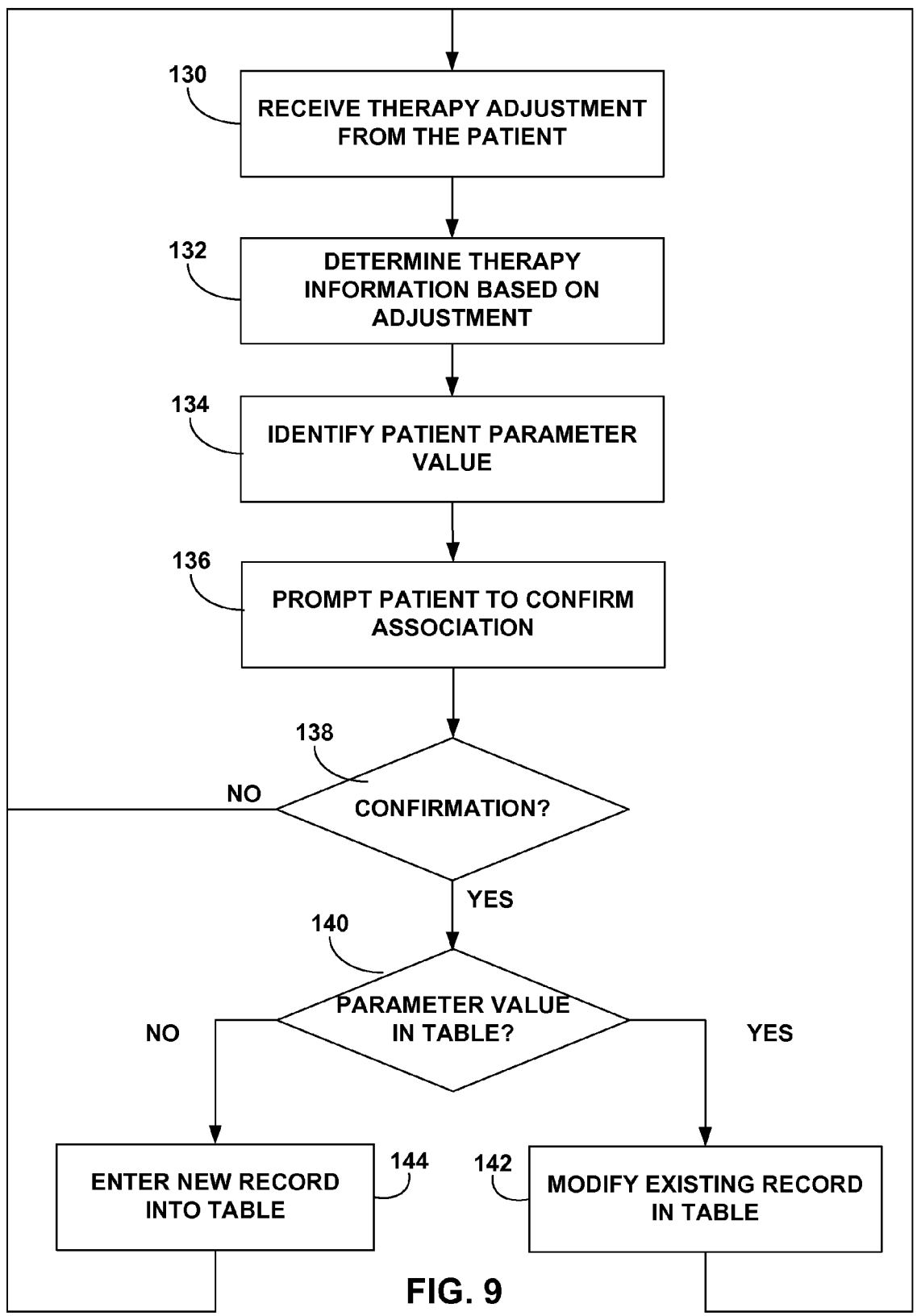
FIG. 9 is a flow diagram illustrating another example technique for associating therapy information with patient parameter values in response to therapy adjustments.

FIG. 9 is a flow diagram illustrating another example technique for associating therapy information with patient parameter values in response to therapy adjustments. According to the example, processor 34 receives a therapy adjustment from patient 14 (130), and determines therapy information based on the therapy adjustment, as described above (132). Processor 34 also identifies a value of a patient parameter, such as posture or activity level, as described above (134).

In the example of FIG. 9, the patient or other user is then prompted to confirm that the association of the determined therapy information and the patient parameter value should be stored in the table, i.e., that the current therapy is desirable (136). Processor 34 and/or processor 60 of programmer 20 may prompt the patient and receive the confirmation via a user interface, such as user interface 62 or programmer 20. This confirmation may be provided in some embodiments as an alternative to automatically entering new associations in the table, as was the case in FIG. 5, to, for example, allow a patient time to evaluate the efficacy of a therapy adjustment prior to creating a record in the table based on the adjustment. If confirmation is received from the patient or other user (138), processor 34 may determine whether the value of the patient parameter is already found in the table (140), and either modify an existing record (142) or enter a new record (144) in the table as described above.

Figure 10:
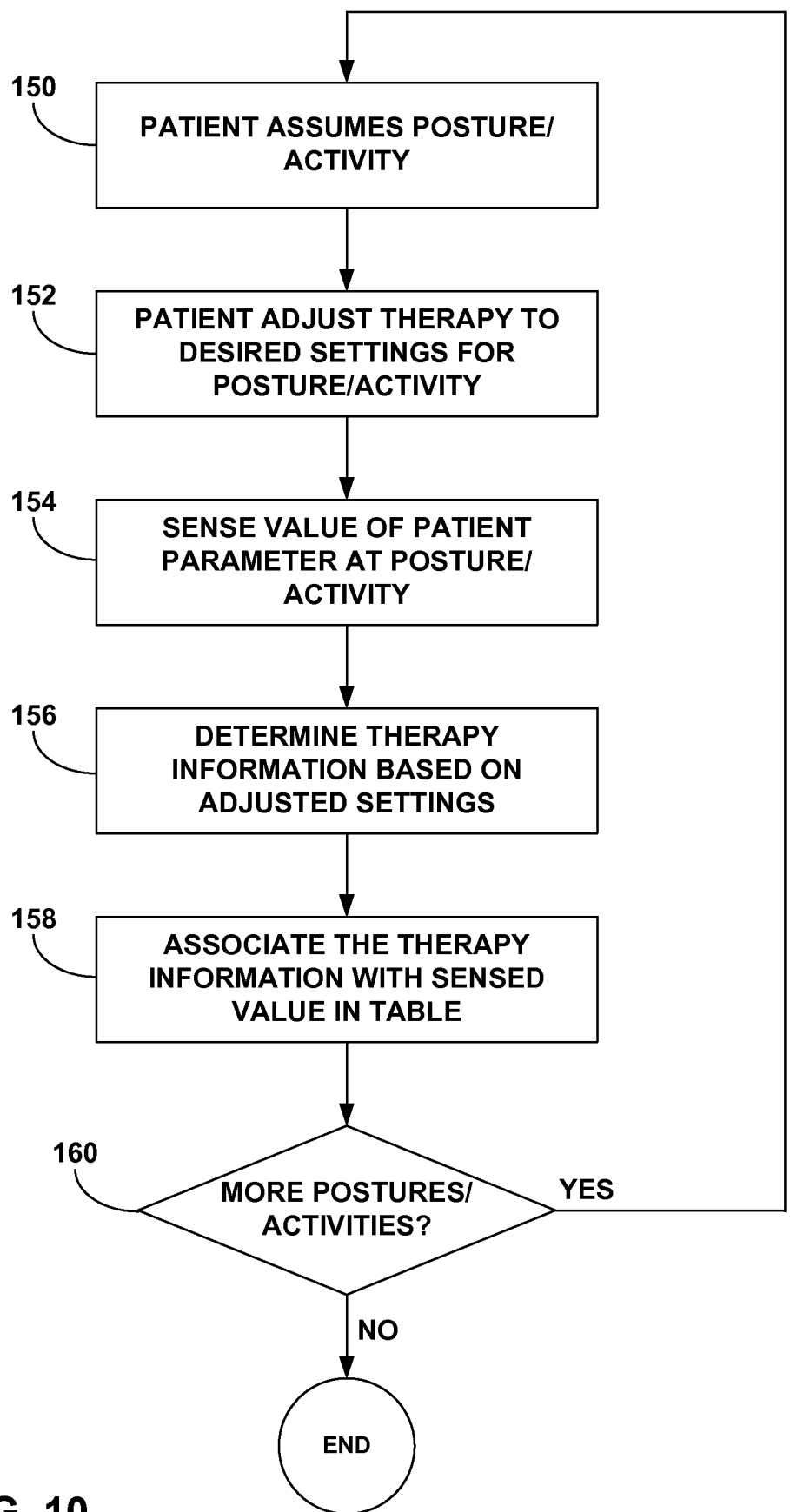
FIG. 10 is a flow diagram illustrating an example technique for associating therapy information with patient parameter values while the patient assumes a plurality of postures or activities.

FIG. 10 is a flow diagram illustrating an example technique for associating therapy information with patient parameter values while the patient assumes a plurality of postures or activities. In some embodiments, it may be desirable for a patient, with or without clinician assistance, to initially fill in a significant portion of the table for a range of patient parameter values, e.g., postures or activities, in a structured or concerted manner. In other words, rather then only populating the table as activities or postures are naturally assumed by the patient, it may be desirable for patient to intentionally assume a range of activities and postures during one or more sessions to populate the table with efficacious therapies.

According to the example of FIG. 10, patient 14 assumes a posture or activity (150). While the patient is assuming the posture or activity, patient 14 or another user, e.g., a clinician, may then adjust therapy as necessary to achieve a desired setting for the assumed posture or activity (152). Processor 34 may then sense a value of the patient parameter while the patient is within the posture or engaged in the activity (154). For example, processor 34 may receive signals indicating posture or activity from a sensor, such as a multi-axis accelerometer. Processor 34 also determines therapy information based on the therapy adjustment made with the patient in the posture or activity (156), and associates the therapy information with the sensed value of the patient parameter, e.g., the value generated by the multi-axis accelerometer (158). The association may be automatic or based on patient confirmation, as discussed above. This process may continue so long as the patient wishes to continue assuming postures and/or activities (160).

The postures and activities may be predetermined, and may have been selected to cover a desired range of posture and activities. In some cases, the tested postures and activities may be selected to reflect the lifestyle of the patient. Further, in some embodiments, the testing of postures and activities may be directed by a clinician, IMD or programming device.

Figure 11:
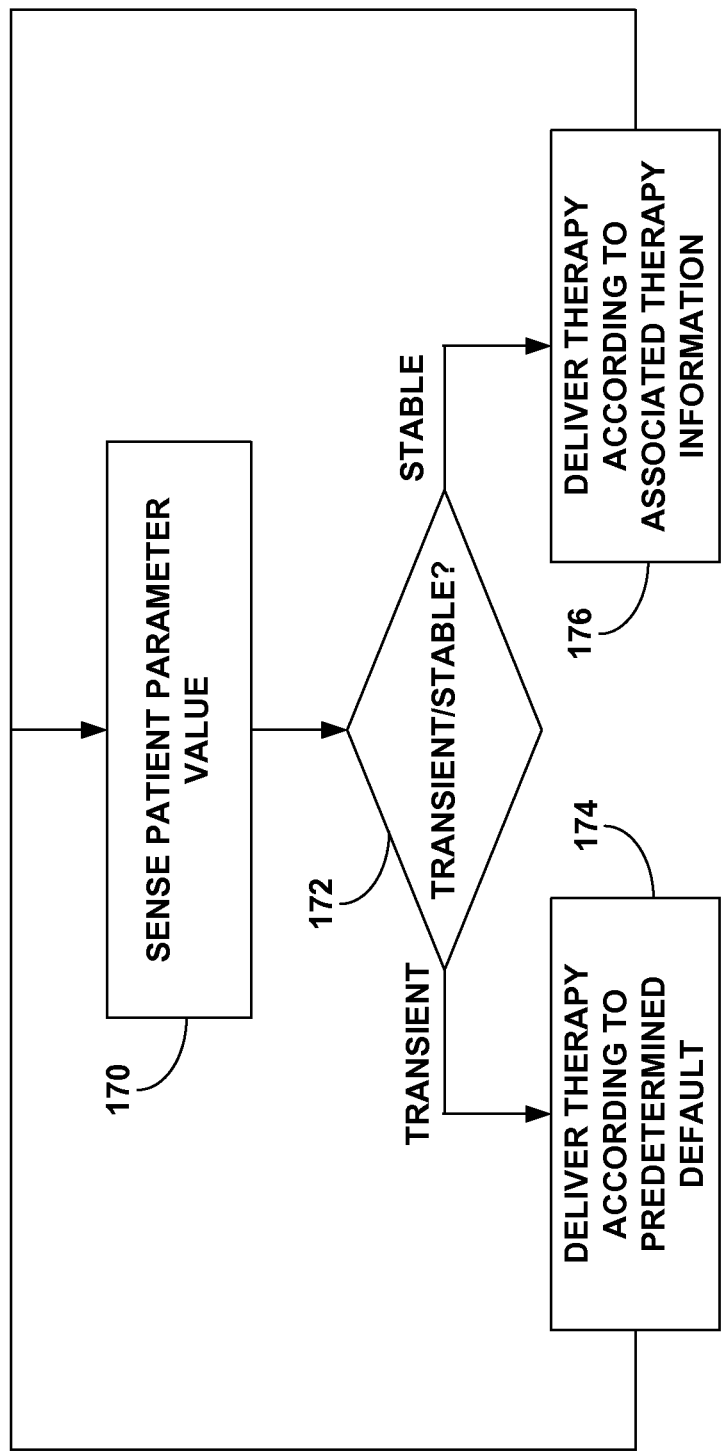
FIG. 11 is a flow diagram illustrating an example technique for delivering stimulation according to associations of therapy information and parameter values or a predetermined default based on whether the parameter values are stable or transient.

FIG. 11 is a flow diagram illustrating an example technique for delivering stimulation according to either therapy information associated with patient parameter values, or predetermined default therapy information, based on whether the patient parameter values are stable or transient. When delivering therapy from IMD 12 based on therapy information/patient parameter value associations, there may be a delay, or "lag," prior to identifying the correct therapy information for a particular patient parameter value. Thus, when the patient parameter is rapidly changing, e.g., when the patient is quickly transitioning between activities or postures, the therapy may be inappropriate for a short period of time prior to identifying the correct therapy information. Inappropriate therapy may cause, for example, patient discomfort.

To avoid delivering inappropriate therapy, IMD 12 may instead deliver a predetermined, default, known-safe therapy, or suspend therapy, during times in which the patient parameter is rapidly and/or transiently changing. According to the example of FIG. 11, processor 34 senses the one or more patient parameter values (170). Processor 34 then determines whether the patient parameter values are transient or stable (172). For example, processor 34 may determine whether the rate of change of the parameter values exceeds a threshold.

If the patient parameter is transient, e.g., rapidly changing, processor 34 controls delivery of therapy according to predetermined, default therapy information, which may include low values for therapy parameters such as amplitude, pulse width, or pulse rate, for a predetermined period of time (174). In other embodiments, the predetermined, default therapy information may cause processor 34 to suspend delivery of therapy for a period of time. The predetermined period of time may be chosen such that the patient parameter is likely to be stable at the end of the period, e.g., the patient is likely to be stably within the new posture or activity. If the patient parameter value is stable, e.g., the rate of change is below the threshold, processor 34 may control delivery of therapy according to therapy information associated with the stable value in the table or other data structure.

Various embodiments of the described invention may include processors that are realized by microprocessors, Application-Specific Integrated Circuits (ASIC), Field-Programmable Gate Arrays (FPGA), or other equivalent integrated or discrete logic circuitry. A processor may also utilize several different types of data storage media to store computer-readable instructions for device operation. These memory and storage media types may include any form of computer-readable media such as magnetic or optical tape or disks, solid state volatile or non-volatile memory, including random access memory (RAM), read only memory (ROM), electronically programmable memory (EPROM or EEPROM), or flash memory. Each storage option may be chosen depending on the embodiment of the invention.

Many embodiments of the invention have been described. However, one skilled in the art will appreciate that various modification may be made to the described embodiments without departing from the scope of the invention. For example, the invention is not limited to medical devices that deliver neurostimulation therapy or to implantable medical devices. Rather, systems that facilitate automatic therapy adjustment according to the invention may include one or more implantable or external medical devices, of any type, that deliver therapy to a patient. For example, in some embodiments, an implantable or external pump that delivers a therapeutic agent to a patient can provide automatic therapy adjustment according to the invention. Further, as discussed above, a programming device, rather than the therapy delivering device, may provide closed-loop therapy adjustments according to the techniques of the invention.

Additionally, in some embodiments, a system that facilitates automatic therapy adjustment does not include a programming device at all. Where a system includes an external medical device that provides therapy to a patient, for example, a user may interact with a user interface provided by the medical device and a programming device may therefore be unnecessary. A user may also interact with an implanted medical device using a magnetic activator, or by tapping over the implanted medical device, which may be detected via an accelerometer, as is known in the art. These and other embodiments are within the scope of the following claims.

The invention claimed is:

1. A method comprising:
receiving a therapy adjustment from a user, wherein the therapy adjustment received from the user comprises an adjustment of a value of at least one parameter of a therapy delivered to a patient by a medical device;
determining a value of a patient parameter in response to the receipt of the therapy adjustment from the user, wherein the patient parameter is sensed via a sensor and is indicative of at least one of patient posture or patient activity;
updating a table in response to the receipt of the therapy adjustment, the table comprising a plurality of records stored in a data structure, each record of the plurality comprising at least one value of the patient parameter and associated therapy information, the therapy information including the at least one parameter, wherein updating the table comprises associating the value of the patient parameter with the value of the at least one parameter; and
delivering the therapy to the patient via the medical device, wherein the therapy is delivered according to a respective record of the plurality of records that is associated with a currently sensed value of the patient parameter, wherein receiving, determining, updating, and delivering are performed using one or more processors.

2. The method of claim 1, wherein updating the table comprises:
modifying an existing record with the therapy adjustment if the value of the patient parameter is already in the table; and
entering a new record associating the therapy adjustment with the value of the patient parameter if the value of the patient parameter is not already in the table.

3. The method of claim 2, wherein the value of the patient parameter is already in the table if the value of the patient parameter is substantially equivalent to an existing value in the table.

4. The method of claim 1, wherein the sensor comprises an accelerometer.

5. The method of claim 1, wherein the patient parameter is indicative of patient posture.

6. The method of claim 1, wherein the patient parameter is indicative of patient activity.

7. The method of claim 1, further comprising directing the patient to assume a plurality of postures or activities via an external device to populate the table.

8. The method of claim 1, wherein the therapy comprises neurostimulation therapy.

9. The method of claim 8, wherein the at least one therapy parameter comprises at least one of a pulse amplitude, a pulse width, a pulse frequency, and an electrode configuration.

10. The system of claim 8, wherein the at least one therapy parameter comprises at least one of a pulse amplitude, a pulse width, a pulse frequency, and an electrode configuration.

11. A system comprising:
a medical device configured to deliver therapy to a patient;
a sensor configured to sense a patient parameter, wherein the patient parameter is indicative of at least one of patient posture or patient activity; and
at least one processor configured to:
receive a therapy adjustment from a user, wherein the therapy adjustment received from the user comprises an adjustment of a value of at least one parameter of a therapy delivered to a patient by a medical device;
determine a value of the patient parameter sensed via the sensor in response to the receipt of the therapy adjustment from the user;
update a table in response to the receipt of the therapy adjustment, the table comprising a plurality of records stored in a data structure, each record of the plurality comprising at least one value of the patient parameter and associated therapy information, the therapy information including the at least one parameter, wherein the processor updates the table by at least associating the value of the patient parameter with the value of the at least one parameter; and
control the delivery of the therapy to the patient via the medical device, wherein the processor controls the delivery of therapy according to a respective record of the plurality of records that is associated with a currently sensed value of the patient parameter.

12. The system of claim 11, wherein the at least one processor is configured to update the table by at least:
modifying an existing record with the therapy adjustment if the at least one processor determines that the value of the patient parameter is already in the table; and
entering a new record associating the therapy adjustment with the value of the patient parameter if the at least one processor determines that the value of the patient parameter is not already in the table.

13. The system of claim 12, wherein the at least one processor determines that the value of the patient parameter is already in the table by at least determining that the value of the patient parameter is substantially equivalent to an existing value in the table.

14. The system of claim 11, wherein the sensor comprises an accelerometer sensor.

15. The system of claim 11, wherein the patient parameter is indicative of patient posture.

16. The system of claim 11, wherein the patient parameter is indicative of patient activity.

17. The system of claim 11, wherein the at least one processor is configured to direct the patient to assume a plurality of postures or activities via an external device to populate the table.

18. The system of claim 11, wherein the therapy comprises neurostimulation therapy.

19. The system of claim 11, wherein the medical device comprises an implantable medical device.

20. A system comprising:
means for receiving a therapy adjustment from a user, wherein the therapy adjustment received from the user comprises an adjustment of a value of at least one parameter of a therapy delivered to a patient by a medical device;
means for determining a value of a patient parameter in response to the receipt of the therapy adjustment from the user, wherein the patient parameter is sensed via a sensor and is indicative of at least one of patient posture or patient activity;
means for updating a table in response to the receipt of the therapy adjustment, the table comprising a plurality of records stored in a data structure, each record of the plurality comprising at least one value of the patient parameter and associated therapy information, the therapy information including the at least one parameter, wherein updating the table comprises associating the value of the patient parameter with the value of the at least one parameter; and
means for delivering the therapy to the patient via the medical device, wherein the therapy is delivered according to a respective record of the plurality of records that is associated with a currently sensed value of the patient parameter.

* * * * *